United States Patent
Jung et al.

(10) Patent No.: US 11,358,913 B2
(45) Date of Patent: Jun. 14, 2022

(54) METHOD FOR OLIGOMERIZING OLEFINS

(71) Applicants: SK Innovation Co., Ltd., Seoul (KR); SK Global Chemical Co., Ltd., Seoul (KR)

(72) Inventors: Woosung Jung, Daejeon (KR); Chansaem Park, Daejeon (KR); Hyoseung Park, Daejeon (KR); Sungreal Son, Daejeon (KR); Inhyoup Song, Daejeon (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 0 days.

(21) Appl. No.: 16/649,916

(22) PCT Filed: Sep. 10, 2018

(86) PCT No.: PCT/KR2018/010533
§ 371 (c)(1),
(2) Date: Mar. 23, 2020

(87) PCT Pub. No.: WO2019/107713
PCT Pub. Date: Jun. 6, 2019

(65) Prior Publication Data
US 2020/0308082 A1    Oct. 1, 2020

(30) Foreign Application Priority Data

Nov. 30, 2017 (KR) .................. 10-2017-0162909

(51) Int. Cl.
*C07C 2/32* (2006.01)
*C07C 7/04* (2006.01)
(Continued)

(52) U.S. Cl.
CPC ............... *C07C 2/32* (2013.01); *B01J 31/143* (2013.01); *B01J 31/2295* (2013.01); *C07C 7/04* (2013.01); *C07C 7/12* (2013.01); *B01J 2231/20* (2013.01); *B01J 2531/62* (2013.01); *C07C 2531/14* (2013.01); *C07C 2531/22* (2013.01)

(58) Field of Classification Search
None
See application file for complete search history.

(56) References Cited

U.S. PATENT DOCUMENTS 8,809,613 B2   8/2014  Fritz et al.
9,375,708 B2   6/2016  Kreischer et al.
(Continued)

FOREIGN PATENT DOCUMENTS

EP         2354113 A1    8/2011
KR    1020100063444 A    6/2010
(Continued)

*Primary Examiner* — Philip Y Louie
(74) *Attorney, Agent, or Firm* — The Webb Law Firm

(57) ABSTRACT

The present invention relates to a method for oligomerizing olefins including the steps of: carrying out an oligomerization reaction of olefins by injecting an oligomerization transition metal catalyst, a cocatalyst, an olefin monomer and a solvent into a reactor; and injecting, into the reaction product of the oligomerization reaction, a catalyst inactivator including a gaseous inorganic material that contains oxygen.

12 Claims, 1 Drawing Sheet

(51) Int. Cl.
    *C07C 7/12*     (2006.01)
    *B01J 31/14*    (2006.01)
    *B01J 31/22*    (2006.01)

(56) References Cited

U.S. PATENT DOCUMENTS

| | | |
|---|---|---|
| 9,598,329 B2 | 3/2017 | Shaik et al. |
| 10,471,416 B2 | 11/2019 | Im et al. |
| 10,508,065 B2 | 12/2019 | Zilbershtein et al. |
| 2007/0185357 A1 | 8/2007 | De Boer et al. |
| 2008/0027188 A1* | 1/2008 | Small ............... B01J 31/143 526/113 |
| 2013/0303817 A1* | 11/2013 | Shaik ............... C07C 2/30 585/504 |
| 2015/0291486 A1* | 10/2015 | Weber ............... C07C 2/30 585/512 |
| 2015/0330706 A1* | 11/2015 | Vermeiren ............ C07C 7/12 62/620 |
| 2017/0305811 A1* | 10/2017 | Shin ................. B01J 31/04 |
| 2019/0308178 A1 | 10/2019 | Lee et al. |

FOREIGN PATENT DOCUMENTS

| | | |
|---|---|---|
| KR | 1020110090900 A | 8/2011 |
| KR | 1020120050963 A | 5/2012 |
| KR | 1020150016961 A | 2/2015 |
| KR | 1020160099478 A | 8/2016 |
| KR | 1020170055149 A | 5/2017 |
| KR | 1020170100579 A | 9/2017 |
| KR | 1020170134045 A | 12/2017 |
| WO | 2007057458 A1 | 5/2007 |

\* cited by examiner

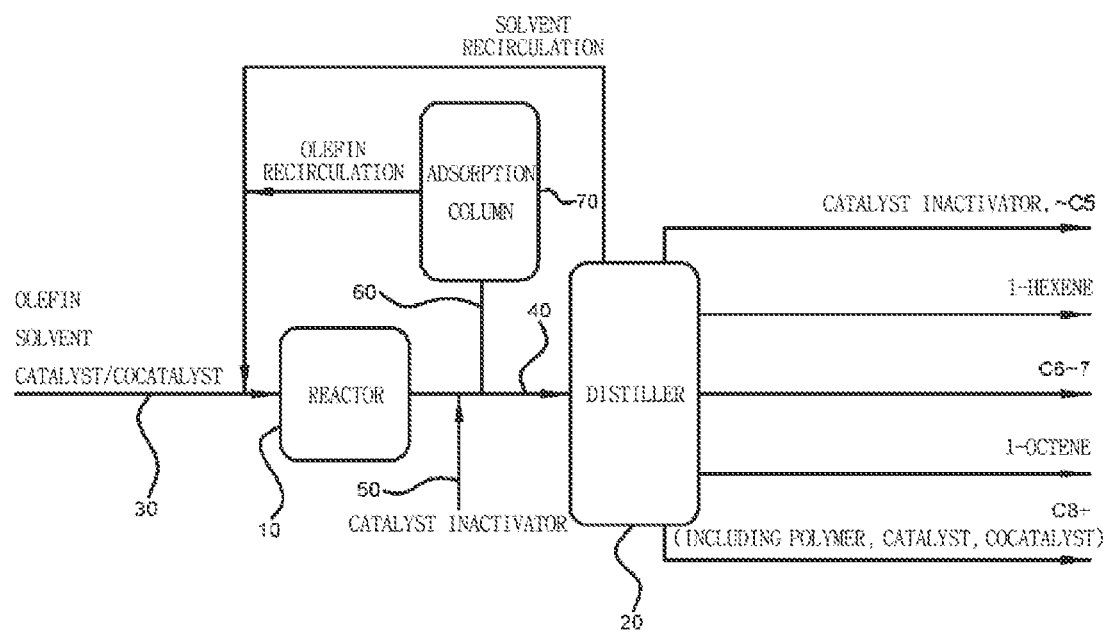

METHOD FOR OLIGOMERIZING OLEFINS

CROSS-REFERENCE TO RELATED APPLICATIONS

This application is the United States national phase of International Application No. PCT/KR2018/010533 filed Sep. 10, 2018, and claims priority to Korean Patent Application No. 10-2017-0162909 filed Nov. 30, 2017, the disclosures of which are hereby incorporated by reference in their entirety.

TECHNICAL FIELD

The present invention relates to a method for oligomerizing olefins.

BACKGROUND ART

Ethylene is a raw material used as a basic material in the chemical industry to such an extent that its production and consumption are considered as indicators of the chemical industry scale of a country. Typically, ethylene has been used as a monomer for preparing polymers such as polyethylene, and the like. In some cases, linear alpha olefins (LAOs) having an approximately C4-C40 carbon length (or chain) are prepared by adjusting a degree of polymerization of ethylene, and thus are used to prepare a variety of chemicals.

The reason why an LAO preparation technique is important is that LAO is a chemical that does not contain sulfur and nitrogen derived from crude oil. Typically, since crude oil contains impurities such as sulfur and nitrogen components in amounts of several percent by weight, it is difficult to directly prepare chemicals composed of pure hydrocarbons without such impurities.

However, ethylene resulting from a catalytic cracking reaction of crude oil may be converted into LAOs, which are in turn converted into desired chemicals, thereby obtaining chemicals composed of pure hydrocarbons without impurities.

An ethylene polymerization reaction is mainly carried out using a batch reactor under air-sensitive conditions in the presence of a metallocene catalyst. Because the metallocene catalyst is a catalyst that has a very strong single acid site, ethylene is selectively polymerized at the single acid site of the catalyst. Due to such properties, a polymer is linearly grown at the acid site of the catalyst. As a result, olefins produced by an LAO preparation reaction have a linear alpha-olefin structure having an even number of carbon atoms because ethylene is used as a monomer.

Linear alpha olefins produced by an LAO preparation process exhibit distinct physical properties depending on the number of carbon atoms thereof, and chemicals prepared therefrom also have distinct physical properties depending on the type of LAO source materials. For example, C4 LAOs obtained by polymerizing two ethylene monomers are present in a gas phase, and polymers resulting from the polymerization thereof have an excessive amount of intramolecular branches, which makes it difficult to apply to a specific product, for example, a lube base oil. Meanwhile, even when C6 LAOs obtained by polymerizing three ethylene monomers are also converted into polymers, it is difficult to apply such polymers to a lube base oil, and the like base oil because the polymers have many intramolecular branches. However, when ethylene is copolymerized with a C6 LAO, an ethylene-1-hexene copolymer having different physical properties from conventional polyethylene may be prepared. C8 LAOs obtained by polymerizing four ethylene monomers may be applied to a Group IV lube base oil via polymerization, and may be used to prepare a copolymer with ethylene, as in the C6 LAOs. Also, C10-C12 LAOs are polymerized, and thus mainly used as the Group IV base oil, and C14-C16 LAOs are reacted with amine or succinic acid so that the resulting reaction products can be applied to various functional chemicals, or can be mixed and applied to inexpensive drilling fluids, and the like. Also, C18 or more LAOs may be used in the form of an additive or wax for lubricants.

Meanwhile, 2-ethylhexanol has been commonly used as the catalyst inactivator for suppressing side reactions at the rear end of the reactor after the ethylene oligomerization reaction. The 2-ethylhexanol has good catalyst inactivation efficiency, but has a problem in that, when it is distilled at the latter part of the process, it is difficult to separate it from certain LAO components.

As a specific example, because 2-ethylhexanol has a problem in that it is not easily phase-separated from C10 LAOs, an additional reactor is needed or severe reaction conditions are required in order to separate the C10 LAOs from the oligomerization reaction product, resulting in increased processing costs as well as degraded separation efficiency.

Accordingly, there is a need for a process for preparing a linear alpha olefin by an ethylene oligomerization reaction capable of separating the reaction products with high separation efficiency while ensuring sufficient catalyst inactivation after the reaction.

DISCLOSURE

Technical Problem

An object of the present invention is to provide a method for preparing a linear alpha olefin (LAO) from olefins capable of preparing high-purity LAOs in an economical manner by suppressing unnecessary side reactions at the rear end of a reactor to prepare linear alpha olefins with high purity and yield and simultaneously separate the prepared LAOs with high separation efficiency.

Technical Solution

In one general aspect, a method for oligomerizing olefins includes: introducing an oligomerization transition metal catalyst, a cocatalyst, an olefin monomer, and a solvent to a reactor to perform an olefin oligomerization reaction; and introducing a catalyst inactivator, which includes an oxygen-containing inorganic material in a gas phase, to a reaction product of the oligomerization reaction.

The oxygen-containing inorganic material may be in a gas phase at 25° C. and 1 atmospheric pressure (atm).

The oxygen-containing inorganic material may be $O_2$, $CO_2$, CO, H2O, $NO_x$, $SO_x$ or a mixture thereof.

The oxygen-containing inorganic material may be $O_2$ or $CO_2$.

The catalyst inactivator may include 0.5 to 100% by weight of the oxygen-containing inorganic material.

The introducing of the catalyst inactivator may be performed at 80° C. to 100° C.

After the introducing of the catalyst inactivator, the method may further include subjecting a gel- or solid-phase component including an inactivated catalyst to solid-liquid separation.

After the introducing of the catalyst inactivator, the method may further include separating an unreacted catalyst inactivator by distillation or adsorption.

The method may further include recirculating the reaction product, which includes an unreacted olefin monomer in the introducing of the catalyst inactivator, to perform the oligomerization reaction.

In the recirculating of the reaction product, the catalyst inactivator in the reaction product including the unreacted olefin monomer may be removed by adsorption.

1-Octene may be included at 30% by weight or more, based on 100% by weight of linear alpha olefins in the reaction product of the oligomerization reaction.

The cocatalyst may be an aluminum compound, an organoaluminoxane, an organoboron compound, or a mixture thereof.

An amount of the introduced catalyst inactivator may be such an amount that an amount of the oxygen-containing inorganic material in the catalyst inactivator is 1 to 50 times higher than the total number of moles of aluminum, boron, or a combination thereof in the cocatalyst based on the number of moles.

The transition metal catalyst may be represented by $ML^1(L^2)_p(X)_q$, or $M_2X^1_2L^1_2(L^2)_y(X)_z$ (wherein M is a transition metal, $L^1$ is a heteroligand, $L^2$ is an organic ligand, X and $X^1$ are each independently a halogen, p is an integer of 0 or 1 or more, q is an integer of (oxidation number of M–p), y is an integer of 2 or more, and z is an integer of (2×oxidation number of M)–y).

The olefin monomer may be ethylene, and oligomers may include a mixture of C4-C40 linear alpha olefins.

Advantageous Effects

According to the method for oligomerizing olefins according to one aspect of the present invention, linear alpha olefins can be prepared with high purity and yield by suppressing unnecessary side reactions at the rear end of a reactor or at the end of a reaction.

At the same time, process energy can also be reduced and process efficiency can be enhanced by separating the prepared LAOs with high separation efficiency, and the LAOs having minimized impurities can be prepared.

DESCRIPTION OF DRAWING

The Figure is an exemplary schematic diagram of a plant capable of performing a method for oligomerizing olefins according to one aspect of the present invention.

BEST MODE

Unless particularly defined otherwise, all terms (including technical and scientific terms) used herein may be used as the same meaning as commonly understood by one of ordinary skill in the art to which this invention belongs. Throughout the specification, a certain part "including" a certain element signifies that the certain part may further include, instead of excluding, another element unless particularly indicated otherwise. Also, the singular forms "a," "an," and "the" include plural referents unless the context clearly dictates otherwise.

One aspect of the present invention provides a method for oligomerizing olefins, which includes: introducing an oligomerization transition metal catalyst, an olefin monomer, and a solvent and performing an olefin oligomerization reaction to produce oligomers; and introducing a catalyst inactivator to a reaction product of the oligomerization reaction to inactivate the catalyst, wherein the catalyst inactivator is in a gas phase at 25° C. and 1 atmospheric pressure (atm), and includes an oxygen-containing inorganic material.

The method for oligomerizing olefins according to one aspect of the present invention may include introducing a catalyst inactivator at the end of the oligomerization reaction, wherein the catalyst inactivator is in a gas phase at 25° C. and 1 atmospheric pressure (atm), and may include the oxygen-containing inorganic material. Therefore, reaction selectivity of the oligomerization reaction may be improved. The reaction selectivity of the oligomerization reaction may be evaluated using the purity of 1-octene in the reaction product, and 1-octene is an expensive material that may be applied to Group IV lube base oil via polymerization and may also be used to prepare a copolymer with ethylene, as in the C6 LAOs. Therefore, the high purity of 1-octene makes it possible to achieve a high added value of the reaction.

Also, the catalyst inactivator, which is in a gas phase at 25° C. and 1 atmospheric pressure (atm) and includes the oxygen-containing inorganic material, may be added, during an oligomerization reaction, to suppress side reactions that occur unnecessarily at the rear end of the reactor or at the end of the reaction, thereby improving the yield of C4-C40 linear alpha olefins. Also, when such a catalyst inactivator is used to separate the produced linear alpha olefin by distillation, and the like in subsequent processes, the final yield of the produced linear alpha olefins may be further improved as a result of improvement of efficiency of separation of the linear alpha olefins from the catalyst inactivator. More specifically, the final yield of 1-octene may be improved to enhance a high added value of the entire processes.

More specifically, when the produced linear alpha olefins are separated by distillation in the subsequent processes, the catalyst inactivator that is in a gas phase at 25° C. and 1 atmospheric pressure (atm) may be separated from the produced linear alpha olefins with high efficiency only by applying low process energy. In this case, the linear alpha olefins may be separated from the catalyst inactivator with high purity.

As a result, a problem of needing an additional reactor or requiring severe reaction conditions in order to separate desired linear alpha olefins from the catalyst inactivator, and the like in the oligomerization reaction product may be solved. Also, separation efficiency of the linear alpha olefins may be improved to remarkably reduce process energy and a process time.

As can be seen from Examples described below, because the boiling point of 2-ethylhexanol that has been used as the conventional catalyst inactivator is distributed between the linear alpha olefin components to be separated, an additional reactor (for example, an additional distillation column) is required to separate 2-ethylhexanol from the linear alpha olefin component having a boiling point similar to the 2-ethylhexanol. As a result, an increase in plant costs, operational costs, and maintenance costs of the process, and an increase in energy load of the entire process may be caused, resulting in degraded economic feasibility of the process.

As a non-limiting example, the oxygen-containing inorganic material may be $O_2$, $CO_2$, CO, $H_2O$, $NO_x$, $SO_x$, or a mixture thereof. Specifically, the oxygen-containing inorganic material may be $O_2$, $CO_2$, CO, or a mixture thereof, and more specifically $CO_2$ and $O_2$. Even more specifically, because $CO_2$ is a material that is generated as a byproduct or an exhaust gas in many fields of industry, and is purchasable at a low cost, it is desirable in terms of improving the economic feasibility of the process.

Here, the $NO_x$ may be, for example, $NO$, $NO_2$, $N_2O$, $N_2O_3$, $N_2O_4$, $N_2O_5$, or a mixture thereof, but the present invention is not limited thereto.

The $SO_x$ may be $SO_2$, $SO_3$, or a mixture thereof, but the present invention is not limited thereto.

In addition to the oxygen-containing inorganic material, the catalyst inactivator may further include another inorganic material that is in a gas phase at 25° C. and 1 atmospheric pressure (atm). For example, the catalyst inactivator may further include an inert gas such as $N_2$, Ar, He, and the like. However, the catalyst inactivator of the present invention includes the oxygen-containing inorganic material that is in a gas phase at 25° C. and 1 atmospheric pressure (atm), and thus may be used without limitation as long as it does not cause other side reactions in the olefin oligomerization reaction, but the present invention is not limited thereto.

The catalyst inactivator includes 0.5 to 100% by weight of the oxygen-containing inorganic material, and may include the balance (by weight) of the another material that is in a gas phase at 25° C. and 1 atmospheric pressure (atm) and does not cause other side reactions in the olefin oligomerization reaction. More specifically, the catalyst inactivator may include 1 to 100% by weight, 2 to 50% by weight, or 3 to 30% by weight of the oxygen-containing inorganic material, but the present invention is not particularly limited thereto.

Such inactivating of the catalyst may be performed at 50° C. to 150° C., and more specifically 80° C. to 100° C. When the catalyst inactivator is introduced and the inactivation reaction is performed in this range of temperature conditions, a reaction product between the catalyst inactivator and the cocatalyst is extracted as a precipitate, or a phenomenon in which the rear end of the reactor is plugged due to aggregation of polymer products having lots of carbon atoms may be prevented.

The inactivation reaction may be performed at a pressure of an atmospheric pressure to 500 bar, specifically a pressure of an atmospheric pressure to 100 bar, and more specifically a pressure of an atmospheric pressure to 80 bar, but the present invention is not limited thereto.

After the inactivating of the catalyst, the method for oligomerizing olefins according to one aspect of the present invention may further include subjecting a gel- or solid-phase component including an inactivated catalyst to solid-liquid separation. The catalyst and/or cocatalyst inactivated by the catalyst inactivator aggregates so that the catalyst and/or cocatalyst can be present in a solid phase as a gel- or solid-phase aggregate in the reaction product. Such a gel- or solid-phase aggregate may be removed by decantation or filtration.

After the inactivating of the catalyst, the method for oligomerizing olefins according to one aspect of the present invention may also further include separating an unreacted catalyst inactivator by distillation or adsorption.

This step is to separate the unreacted catalyst inactivator. In this case, the unreacted catalyst inactivator that is in a gas phase at 25° C. and 1 atmospheric pressure (atm) may be easily separated from the produced linear alpha olefins. Specifically, only low energy may be applied to separate the catalyst inactivator from the produced linear alpha olefin with high efficiency, thereby separating high-purity linear alpha olefins with low processing costs.

Unlike 2-ethylhexanol that has been used as the conventional catalyst inactivator, the catalyst inactivator according to this aspect also has a boiling point different from certain LAOs such as the produced C10 LAOs, and the like. Therefore, because there is no problem of requiring an additional distillation column in order to separate 2-ethylhexanol and certain LAOs such as the produced C10 LAOs, and the like, plant costs, operational costs, and plant maintenance costs may be saved, thereby highly improving economic feasibility of the process.

Further, a concentration of 1-octene in the reaction product finally recovered after this step may be improved, and the quality of the product may be improved accordingly, thereby enhancing a high added value of the entire processes.

When the unreacted catalyst inactivator is separated by distillation, a distiller is not limited to certain types of distillers, the number of distillation column stages may be adjusted when necessary. Also, a distillation method is not limited to certain distillation methods, and proper distillation methods may be used when necessary.

As a non-limiting example, the distiller includes a bottom reboiler and an overhead condenser, and a plurality of distillation columns in which the number of stages is in a range of 50 to 100 may be used.

When the unreacted catalyst inactivator is separated by adsorption, an adsorption column, which is filled with an adsorbent capable of adsorbing the oxygen-containing inorganic material that is included in the catalyst inactivator and is in a gas phase at 25° C. and 1 atmospheric pressure (atm), may be used. The number of adsorption column stages may be adjusted when necessary, but the present invention is not particularly limited thereto. As one non-limiting example of the adsorbent, a metal oxide or zeolite adsorbent may be used as an adsorbent which may remove the oxygen-containing inorganic material by adsorption. As a specific example, copper oxides such as $CuO$, $Cu_2O$, and the like, or zeolite 4A may be used.

Meanwhile, after the inactivating of the catalyst, the method for oligomerizing olefins according to one aspect of the present invention may further include recirculating the reaction product including an unreacted olefin monomer to perform the oligomerization reaction.

In this way, loss of source materials may be minimized, thereby enhancing efficiency of the process. In this step, after the catalyst inactivator included in the reaction product during the inactivating of the catalyst is removed, the reaction product should be recirculated.

In the method for oligomerizing olefins according to one aspect of the present invention, the catalyst inactivator included in the reaction product during the inactivating of the catalyst may be removed using the aforementioned adsorption column in this step.

In the method for oligomerizing olefins according to one aspect of the present invention, because the catalyst inactivator is a material that is in a gas phase at 25° C. and 1 atmospheric pressure (atm), the catalyst inactivator may be removed by adsorption only by passing the catalyst inactivator through an adsorption column charged with an adsorbent capable of adsorbing the catalyst inactivator.

Accordingly, because an additional distillation process that consumes high energy to recirculate unreacted olefins is not performed, processing costs may be greatly saved. Also, because most of the catalyst inactivator may be removed using the adsorbent, a problem of degrading a conversion rate of reaction by the catalyst inactivator present in a recirculation stream while recirculating the unreacted olefins may be solved.

In the present invention, the linear alpha olefins in the reaction product of the oligomerization reaction may be C4-C40 linear alpha olefins, and more specifically C4-C30 or C4-C20 linear alpha olefins.

Even more specifically, the linear alpha olefins may include 30% by weight or more, or 50% by weight or more of 1-octene. Because 1-octene has a wide range of applications and is expensive, 1-octene may enhance a high added value of the olefin oligomerization process when 1-octene is included in this range as described above. Also, 1-octene has an advantage in that, because a content of 1-octene in the linear alpha olefins is high, only 1-octene may be easily separated with high purity even when the high-carbon linear alpha olefins are mixed with the reaction product, but the present invention is not particularly limited thereto.

In the method for oligomerizing olefins according to one aspect of the present invention, the cocatalyst may be further introduced when the oligomerization transition metal catalyst, the olefin monomer, and the solvent are introduced into the reactor to perform an olefin oligomerization reaction.

The cocatalyst may be an organoaluminum compound, an organoaluminoxane, an organoboron compound, or a mixture thereof.

The organoaluminum compound may be an $AlR_3$ compound (wherein R is each independently a (C1-C12)alkyl, a (C2-C10)alkenyl, a (C2-C10)alkynyl, a (C1-C12)alkoxy, or a halogen), or $LiAlH_4$, but the present invention is not limited thereto.

More specifically, the organoaluminum compound may be one selected from trimethylaluminum (TMA), triethylaluminum (TEA), triisobutylaluminum (TIBA), tri-n-octylaluminum, methylaluminum dichloride, ethylaluminum dichloride, dimethylaluminum chloride, diethylaluminum chloride, aluminum isopropoxide, ethylaluminum sesquichloride, and methylaluminum sesquichloride, or a mixture thereof, but the present invention is not limited thereto.

The organoaluminoxane may be an oligomer compound that may be prepared by adding water to trimethylaluminum, but the present invention is not limited thereto. The aluminoxane oligomer compound thus prepared may be linear, cyclic, cage, or a mixture thereof.

Specifically, the organoaluminoxane may be selected from alkylaluminoxanes, for example, methylaluminoxane (MAO), ethylaluminoxane (EAO), tetraisobutylaluminoxane (TIBAO), and isobutylaluminoxane (IBAO), as well as modified alkyl aluminoxanes, for example, modified methylaluminoxane (MMAO). The modified methyl aluminoxane (manufactured by Akzo Nobel) may include a mixed alkyl group such as an isobutyl or n-octyl group in addition to a methyl group, but the present invention is not limited thereto.

More specifically, the organoaluminoxane may be one selected from methylaluminoxane (MAO), modified methylaluminoxane (MMAO), ethylaluminoxane (EAO), tetraisobutylaluminoxane (TIBAO), and isobutylaluminoxane (IBAO), or a mixture thereof, but the present invention is not limited thereto.

The organoboron compound may be boroxine, $NaBH_4$, triethylborane, triphenylborane, a triphenylborane ammonia complex compound, tributylborate, triisopropylborate, tris (pentafluorophenyl)borane, trityl(tetrapentafluorophenyl) borate, dimethylammonium(tetrapentafluorophenyl) borate, diethylphenylammonium(tetrapentafluorophenyl) borate, methyldiphenylammonium(tetrapentafluorophenyl) borate, or ethyldiphenylammonium(tetrapentafluorophenyl) borate, and these organoboron compounds may be used as a mixture with the organoaluminum compound or the organoaluminoxane, but the present invention is not limited thereto.

In the introducing of the catalyst inactivator to inactivate the catalyst, an amount of the introduced catalyst inactivator may be such an amount that an amount of the oxygen-containing inorganic material in the catalyst inactivator is 1.5 to 20 times higher than the total number of moles of aluminum, boron, or a combination thereof in the cocatalyst based on the number of moles. When the catalyst inactivator is introduced in this range, sufficient inactivation of the catalyst may occur, and the catalyst inactivator may be easily separated from the linear alpha olefins in the oligomerization reaction product, but the present invention is not particularly limited thereto. More specifically, The amount of the introduced catalyst inactivator may be such an amount that an amount of the oxygen-containing inorganic material in the catalyst inactivator is 1.5 times to 10 times, 2 times to 8 times, or 3 times to 7 times higher than the total number of moles of aluminum, boron, or a combination thereof in the cocatalyst based on the number of moles.

The method for oligomerizing olefins according to one aspect of the present invention may be performed in a plant including any type of a reactor. The Figure is an exemplary schematic diagram of a plant capable of performing a method for oligomerizing olefins according to one aspect of the present invention. Hereinafter, the method for oligomerizing olefins according to one aspect of the present invention will be described in further detail with reference to the Figure. However, it should be understood that the present invention is not limited to the Figure, and may be freely modified and put into practice by those skilled in the art without departing from the technical scope of the present invention.

A plant may include a reactor 10 configured to perform oligomerization, a feed line 30 configured to feed an olefin and a catalyst composition into the reactor 10, an outlet line 40 configured to allow an oligomerization reaction product to flow out of the reactor 10, a catalyst inactivator feed line 50 configured to introduce a catalyst inactivator through the outlet line 40, a distiller 20 configured to separate the oligomerization reaction product, a recirculation line 60 configured to recirculate unreacted olefins in an effluent discharged through the outlet line 40, and an adsorption column 70 configured to remove the catalyst inactivator from a mixture containing the recirculated unreacted olefins. In this case, the catalyst composition is an olefin oligomerization catalyst composition disclosed in the present invention, and may include a transition metal source and a heteroatom ligand, or an oligomerization transition metal catalyst/cocatalyst prepared therefrom.

The reactor 10 may include a batch-type reactor, a semi-batch-type reactor, and a continuous reactor, but the present invention is not limited thereto.

The distiller 20 is not limited to certain types of distillers, and the number of distillation column stages may be adjusted when necessary. Also, a distillation method is not limited to certain distillation methods, and proper distillation methods may be used when necessary. By way of example, the distiller 20 includes a bottom reboiler (BTM reboiler) and an overhead condenser (OVHD condenser), and a plurality of distillation columns in which the number of stages is in a range of 50 to 100 may be used.

An adsorption column, which is filled with an adsorbent capable of adsorbing an oxygen-containing inorganic material that is included in the catalyst inactivator and is in a gas phase at 25° C. and 1 atmospheric pressure (atm), may be used as the adsorption column 70. The number of adsorption columns may be adjusted when necessary, but the present invention is not particularly limited thereto. As a non-limiting example of the adsorbent, a metal oxide or zeolite adsorbent may be used as an adsorbent which may remove the oxygen-containing inorganic material by adsorption. As a specific example, copper oxides such as CuO, $Cu_2O$, and the like, or zeolite 4A may be used.

The catalyst composition may include a transition metal source and a heteroatom ligand, or an oligomerization transition metal catalyst and cocatalyst prepared therefrom as an oligomerization transition metal catalyst.

In the method for oligomerizing olefins according to one aspect of the present invention, the olefin monomer may be ethylene, and the oligomers may include a mixture of C4-C40 linear alpha olefins, but the present invention is not particularly limited thereto.

In the method for oligomerizing olefins according to one aspect of the present invention, when the oligomerization transition metal catalyst, the olefin monomer, and the solvent are introduced into the reactor, the solvent may be an inert solvent. That is, any inert solvent that does not react with the oligomerization transition metal catalyst, the cocatalyst, and the catalyst inactivator may be used as the solvent, and the inert solvent may include an aliphatic hydrocarbon. The aliphatic hydrocarbon includes saturated aliphatic hydrocarbons, that is, a linear saturated aliphatic hydrocarbon represented by $C_nH_{2n+2}$ (wherein n is an integer ranging from 1 to 15), an alicyclically saturated aliphatic hydrocarbon represented by $C_mH_{2m}$ (wherein m is an integer ranging from 3 to 8), and a saturated aliphatic hydrocarbon substituted with one or two or more lower alkyl groups having 1 to 3 carbon atoms. Examples of the solvent specifically listed herein may include one or more selected from hexane, heptane, octane, nonene, decane, undecane, dodecane, tetradecane, 2,2-dimethylpentane, 2,3-dimethylpentane, 2,4-dimethylpentane, 3,3-dimethylpentane, 2,2,4-trimethylpentane, 2,3,4-trimethylpentane, 2-methylhexane, 3-methylhexane, 2,2-dimethylhexane, 2,4-dimethylhexane, 2,5-dimethylhexane, 3,4-dimethylhexane, 2-methylheptane, 4-methylheptane, cyclohexane, methylcyclohexane, ethylcyclohexane, isopropylcyclohexane, 1,4-dimethylcyclohexane, and 1,2,4-trimethylcyclohexane, but the present invention is not limited thereto.

Also, in the method for oligomerizing olefins according to one aspect of the present invention, the oligomerization reaction may be performed at a reaction temperature, for example, a temperature of 0 to 200° C., specifically a temperature of 15 to 130° C., and even more specifically a temperature of 40 to 100° C., but the present invention is not limited thereto. Also, the oligomerization reaction may be performed at a reaction pressure, for example, a pressure of an atmospheric pressure to 500 bar, specifically a pressure of an atmospheric pressure to 100 bar, and more specifically a pressure of an atmospheric pressure to 80 bar, but the present invention is not limited thereto.

Hereinafter, an olefin oligomerization catalyst of the present invention will be described in detail. However, it should be understood that the oligomerization catalyst of the present invention is not particularly limited thereto.

The olefin oligomerization catalyst may be directly prepared and used, or commercially available oligomerization catalysts may be used herein. Also, components that may be used to prepare an oligomerization catalyst, that is, a transition metal source and a heteroatom ligand may be used.

The transition metal source according to one aspect of the present invention may be an inorganic transition metal salt, an organic transition metal salt, a transition metal coordination compound, or a complex of the transition metal with an organic metal, and a transition metal of the transition metal source may be a Group IV, V or VI transition metal, and specifically chromium, molybdenum, tungsten, titanium, tantalum, vanadium, or zirconium, and preferably chromium.

By way of example, a transition metal of the transition metal source may be bound with various organic ligands, and such organic ligands may be selected from the following structures.

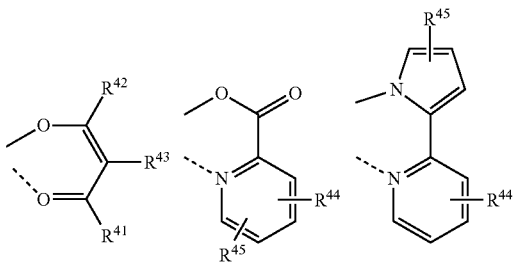

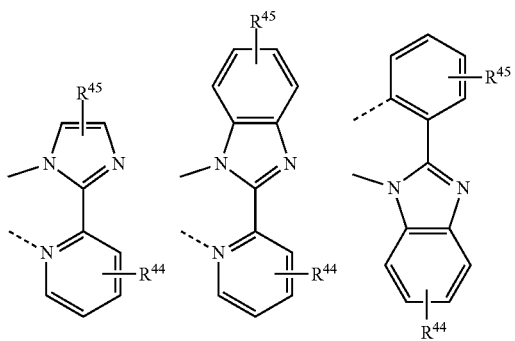

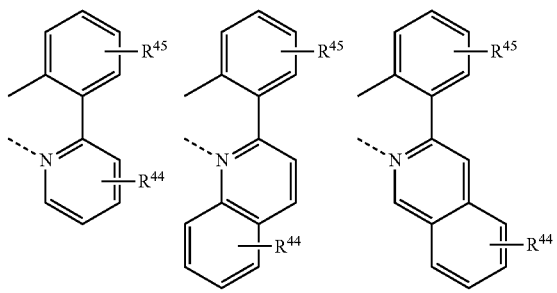

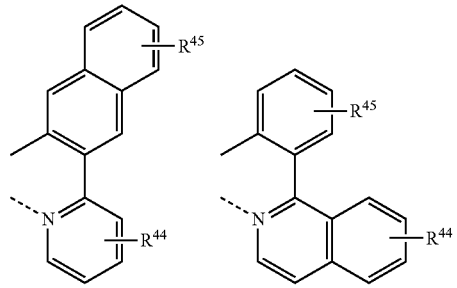

-continued

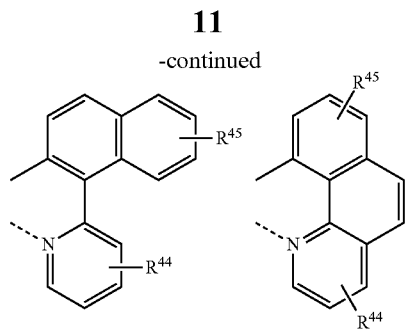

(wherein $R^{41}$ to $R^{45}$ are each independently a hydrocarbyl, a substituted hydrocarbyl, a heterohydrocarbyl, or a substituted heterohydrocarbyl).

The organic ligand may be preferably an acetylacetonato-based ligand represented by the following Formula 2:

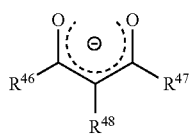

[Formula 2]

(wherein $R^{46}$ to $R^{48}$ are each independently hydrogen, a halogen, a (C6-C20)aryl, a (C6-C20)ar(C1-C10)alkyl, a (C1-C10)alkyl, a halo(C1-C10)alkyl, a (C6-C20)ar(C2-C10)alkenyl, a (C2-C10)alkenyl, a (C6-C20)ar(C2-C10)alkynyl, a (C2-C10)alkynyl, a (C1-C10)alkoxy, a (C6-C20)aryloxy, a (C1-C10)alkylcarbonyloxy, a (C2-C10)alkenylcarbonyloxy, a (C2-C10)alkynylcarbonyloxy, a (C3-C7)cycloalkyl, a (C1-C10)alkylsilyl, a (C2-C10)alkenylsilyl, a (C2-C10)alkynylsilyl substituted with fluorine, a (C6-C20)arylsilyl, a (C3-C20)heteroaryl, or a 5- to 7-membered heterocycloalkyl; and the aryl, the aralkyl, the alkyl, the aralkenyl, the alkenyl, the aralkynyl, the alkynyl, the alkoxy, the aryloxy, the cycloalkyl, the heteroaryl, and the heterocycloalkyl of $R^{46}$ to $R^{48}$ may be further substituted with one or more selected from a (C1-C10)alkyl, a (C2-C10)alkenyl, a (C2-C10)alkynyl, a (C1-C10)alkoxy, a (C6-C20)aryl, a (C6-C20)aryloxy, and a halogen).

Preferably, $R^{46}$ and $R^{47}$ in Formula 2 may be each independently hydrogen, a halogen or a halo(C1-C10)alkyl, and $R^{48}$ may be hydrogen or a (C1-C10)alkyl.

The acetylacetonato-based ligand of Formula 2 according to one exemplary embodiment of the present invention may be selected from the following structures, but the present invention is not limited thereto.

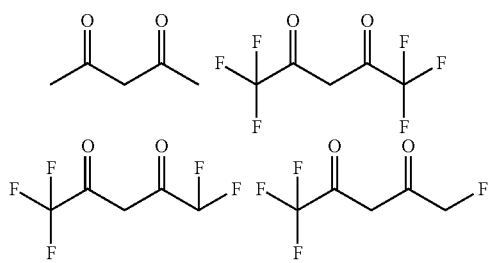

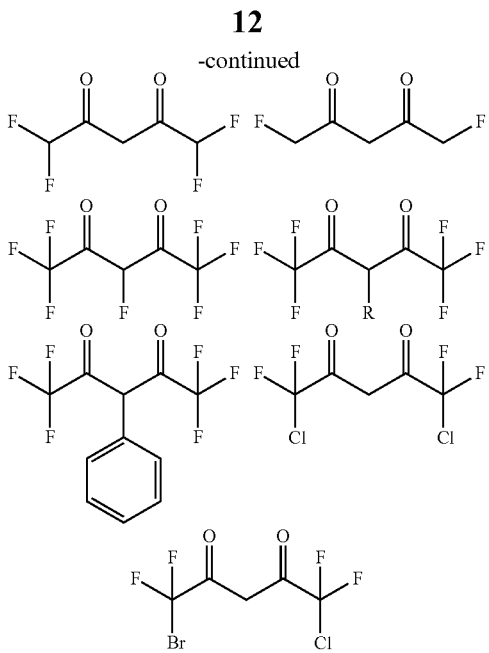

When the transition metal as one specific example of the transition metal source is chromium, the transition metal may include one or two or more selected from chromium (III) acetylacetonate, chromium(III) chloride, chromium(III) naphthenate, chromium(III) 2-ethylhexanoate, chromium (III) acetate, chromium(III) 2,2,6,6-tetramethylheptadionate, chromium(III) octanoate, and chromium hexacarbonyl. Preferably, the transition metal may be chromium(III) acetylacetonate or chromium(III) chloride.

Preferably, the heteroatom ligand according to one exemplary embodiment of the present invention may be $(R)_n$B-C-D$(R)_m$ (wherein B and D are independently any one selected from phosphorus, arsenic, antimony, oxygen, bismuth, sulfur, selenium, and nitrogen, C is a linking group between B and D, R is the same as or different from each other, and is each independently selected from a hydrocarbyl group, a heterohydrocarbyl group, a substituted hydrocarbyl group, and a substituted heterohydrocarbyl group, n and m each may be determined from the valence and oxidation state of either B or D, respectively, B and D are preferably independently phosphorus, C may be a linking group between B and D, that is, alkylene or N(R') (wherein R' is an alkyl), R is the same as or different from each other, and is each independently selected from a hydrocarbyl group, a heterohydrocarbyl group, a substituted hydrocarbyl group, and a substituted heterohydrocarbyl group, and n and m each may be determined from the valence and oxidation state of either B or D, respectively).

The heteroatom ligand may have a P—C—C—P backbone structure represented by the following Formula 3, or a P—N—P backbone structure represented by the following Formula 4, but the present invention is not limited thereto:

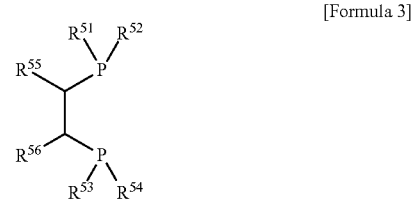

[Formula 3]

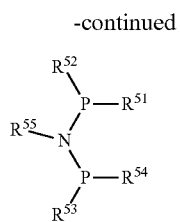

[Formula 4]

(wherein $R^{51}$ to $R^{54}$ are each independently a hydrocarbyl, a substituted hydrocarbyl, a heterohydrocarbyl, or a substituted heterohydrocarbyl;

$R^{55}$ and $R^{56}$ are each independently a hydrocarbyl or a substituted hydrocarbyl, or $R^{55}$ and $R^{56}$ may be taken together via hydrocarbylene, substituted hydrocarbylene, heterohydrocarbylene, or substituted heterohydrocarbylene to form a ring).

$R^{51}$ to $R^{54}$ in Formulas 3 and 4 are each independently a (C6-C20)aryl, a (C6-C20)ar(C1-C10)alkyl, a (C6-C20)ar(C2-C10)alkenyl, a (C6-C20)ar(C2-C10)alkynyl, a (C1-C10)alkyl, a (C2-C10)alkenyl, a (C2-C10)alkynyl, a (C1-C10)alkoxy, a (C6-C20)aryloxy, a (C1-C10)alkoxycarbonyl, a (C1-C10)alkylcarbonyloxy, a (C2-C10)alkenylcarbonyloxy, a (C2-C10)alkynylcarbonyloxy, an aminocarbonyl, a (C1-C10)alkylcarbonylamino, a (C2-C10)alkenylcarbonylamino, a (C2-C10)alkynylcarbonylamino, a (C3-C7)cycloalkyl, a thio(C1-C10)alkyl, a thio(C2-C10)alkenyl, a thio(C2-C10)alkynyl, a (C1-C10)alkylsilyl, a (C2-C10)alkenylsilyl, a (C2-C10)alkynylsilyl, a (C6-C20)arylsilyl, a (C3-C20)heteroaryl, a 5- to 7-membered heterocycloalkyl, or —NR61R62, wherein R61 and R62 are each independently a (C1-C10)alkyl, a (C2-C10)alkenyl, a (C2-C10)alkynyl, a (C6-C20)aryl, a di(C1-C10)alkylamino, a di(C2-C10)alkenylamino, or a di(C2-C10)alkynylamino;

$R^{55}$ and $R^{56}$ are each independently a (C6-C20)aryl, a (C6-C20)ar(C1-C10)alkyl, a (C6-C20)ar(C2-C10)alkenyl, a (C6-C20)ar(C2-C10)alkynyl, a (C1-C10)alkyl, a (C2-C10)alkenyl, a (C2-C10)alkynyl, a (C3-C7)cycloalkyl, a (C3-C20)heteroaryl, a 5- to 7-membered heterocycloalkyl, a (C1-C10)alkoxy, a (C6-C20)aryloxy, a (C1-C10)alkoxycarbonyl, a (C1-C10)alkylcarbonyloxy, a (C2-C10)alkenylcarbonyloxy, a (C2-C10)alkynylcarbonyloxy, an aminocarbonyl, a (C1-C10)alkylcarbonylamino, a (C2-C10)alkenylcarbonylamino, a (C2-C10)alkynylcarbonylamino, a di(C1-C10)alkylamino, a di(C2-C10)alkenylamino, a di(C2-C10)alkynylamino, a (C1-C10)alkylsilyl, a (C2-C10)alkenylsilyl, a (C2-C10)alkynylsilyl, or a (C6-C20)arylsilyl, or $R^{55}$ and $R^{56}$ may be taken together via a (C3-C10)alkylene or a (C3-C10)alkenylene to form a ring; and the aryl, the aralkyl, the aralkenyl, the aralkynyl, the alkyl, the alkenyl, the alkoxy, the aryloxy, the alkoxycarbonyl, the alkylcarbonyloxy, the alkenylcarbonyloxy, the alkynylcarbonyloxy, the cycloalkyl, the heteroaryl, or the heterocycloalkyl of $R^{51}$ to $R^{54}$, and the aryl, the aralkyl, the aralkenyl, the aralkynyl, the alkyl, the alkenyl, the cycloalkyl, the heteroaryl, the heterocycloalkyl, the alkoxy, the aryloxy, the alkoxycarbonyl, the alkylcarbonyloxy, the alkenylcarbonyloxy, the alkynylcarbonyloxy, the aminocarbonyl, the alkylcarbonylamino, the alkenylcarbonylamino, the alkynylcarbonylamino, the dialkylamino, the dialkenylamino, the dialkynylamino, the alkylsilyl, the alkenylsilyl, the alkynylsilyl, or the arylsilyl of $R^{55}$ and $R^{56}$ may be further substituted with one or more selected from a (C1-C10)alkyl, a (C2-C10)alkenyl, a (C2-C10)alkynyl, a (C1-C10)alkoxy, a (C6-C20)aryloxy, a di(C1-C10)alkylamino, a di(C2-C10) alkenylamino, a di(C2-C10)alkynylamino, and a halogen.

Preferably, $R^{51}$ to $R^{54}$ in Formulas 3 and 4 may be each independently a (C6-C20)aryl; and $R^{55}$ and $R^{56}$ may be each independently a (C1-C10)alkyl.

Specifically, in Formulas 3 and 4, $R^{51}$ to $R^{54}$ are each independently phenyl, benzyl, biphenyl, naphthyl, anthracenyl, mesityl, xylyl, methyl, ethyl, ethenyl, ethinyl, n-propyl, i-propyl, propenyl, propynyl, n-butyl, t-butyl, butenyl, butynyl, methylphenyl, ethylphenyl, methoxyphenyl, ethoxyphenyl, isopropylphenyl, isopropoxyphenyl, t-butylphenyl, cumyl, methoxy, ethoxy, phenoxy, tolyloxy, dimethylaminophenyl, cyclopropyl, cyclobutyl, cyclopentyl, cyclohexyl, methylcyclohexyl, ethylcyclohexyl, isopropylcyclohexyl, dimethylamino, thiomethyl, trimethylsilyl, or dimethylhydrazyl;

$R^{55}$ and $R^{56}$ are each independently methyl, ethyl, ethenyl, ethinyl, n-propyl, i-propyl, propenyl, propynyl, n-butyl, t-butyl, i-butyl, butenyl, butynyl, phenyl, benzyl, tolyl, xylyl, methoxy, ethoxy, phenoxy, methylamino, or dimethylamino, or $R^{55}$ and $R^{56}$ may be taken together via propylene, butylene, pentylene, or butenylene to form a 5- to 7-membered ring.

The ligand having the P—C—C—P backbone structure of Formula 3 may be selected from (phenyl)₂P—CH(methyl)CH(methyl)-P(phenyl)₂, (4-methoxyphenyl)₂P—CH(methyl)CH(methyl)-P(4-methoxyphenyl)₂, (4-methylphenyl)₂P—CH(methyl)CH(methyl)-P(4-methylphenyl)₂, (4-ethylphenyl)₂P—CH(methyl)CH(methyl)-P(phenyl)₂, (2-ethylphenyl)₂P—CH(methyl)CH(methyl)-P(2-ethylphenyl)₂, (2-isopropylphenyl)₂P—CH(methyl)CH(methyl)-P-(2-isopropylphenyl)₂, (2-methylphenyl)₂P—CH(methyl)CH(methyl)P-(2-methylphenyl)₂, (2-ethylphenyl)₂P—CH(methyl)CH(methyl)-P(phenyl)₂, (3-methoxyphenyl)₂P—CH(methyl)CH(methyl)-P(3-methoxyphenyl)₂, (4-ethoxyphenyl)₂P—CH(methyl)CH(methyl)-P(2-ethoxyphenyl)₂, (4-dimethylaminophenyl)₂P—CH(methyl)CH(methyl)-P(4-dimethylaminophenyl)₂, (4-ethylcyclohexyl)₂P—CH(methyl)CH(methyl)-P(4-ethylcyclohexyl)₂, (2-methoxyphenyl)₂P—CH(methyl)CH(methyl)-P(2-methoxyphenyl)₂, (2-ethoxyphenyl)₂P—CH(methyl)CH(methyl)-P(2-ethoxyphenyl)₂, (2-dimethylaminophenyl)₂P—CH(methyl)CH(methyl)-P(2-dimethylaminophenyl)₂, (2-ethylcyclohexyl)₂P—CH(methyl)CH(methyl)-P(2-ethylcyclohexyl)₂, (4-ethylphenyl)₂P—CH(ethyl)CH(methyl)-P(4-ethylphenyl)₂, (4-methoxyphenyl)₂P—CH(ethyl)CH(methyl)-P(phenyl)₂, (2-ethylphenyl)₂P—CH(ethyl)CH(methyl)-P(2-ethylphenyl)₂, (4-ethylphenyl)₂P—CH(ethyl)CH(ethyl)-P(4-ethylphenyl)₂, (phenyl)₂P—CH(ethyl)CH(ethyl)-P(phenyl)₂, (2-ethylphenyl)₂P—CH(ethyl)CH(ethyl)-P(2-ethylphenyl)₂, (phenyl)₂P—CH(isopropyl)CH(methyl)-P(phenyl)₂, (4-methoxyphenyl)₂P—CH(isopropyl)CH(methyl)-P(4-methoxyphenyl)₂, (4-ethylphenyl)₂P—CH(isopropyl)CH(methyl)-P(4-ethylphenyl)₂, (2-ethylphenyl)₂P—CH(isopropyl)CH(methyl)-P(2-ethylphenyl)₂, (phenyl)₂P—CH(n-propyl)CH(methyl)-P(phenyl)₂, (4-methoxyphenyl)₂P—CH(n-propyl)CH(methyl)-P(4-methoxyphenyl)₂, (4-ethylphenyl)₂P—CH(n-propyl)CH(methyl)-P(4-ethylphenyl)₂, (2-ethylphenyl)₂P—CH(n-propyl)CH(methyl)-P(2-ethylphenyl)₂, (phenyl)₂P—CH(isopropyl)CH(ethyl)-P(phenyl)₂, (4-methoxyphenyl)₂P—CH(isopropyl)CH(ethyl)-P(4-methoxyphenyl)₂, (4-ethylphenyl)₂P—CH(isopropyl)CH(ethyl)-P(4-ethylphenyl)₂, (2-ethylphenyl)₂P—CH(isopropyl)CH(ethyl)-P(2-ethylphenyl)₂, 1,2-di-(P(phenyl)₂)cyclohexane, 1,2-di-(P(4-methoxyphenyl)₂)cyclohexane, 1,2-di-(P(4-ethylphenyl)₂)cyclohexane, 1,2-di-(P(2-ethylphenyl)₂)cyclohexane, 1,2-di-(P(phenyl)₂)cyclopentane, 1,2-di-(P(4-methoxyphenyl)₂)cyclopentane, 1,2-di-(P(4-ethylphenyl)₂) cyclopentane, 1,2- di-(P(2-ethylphenyl)₂) cyclopentane, (4-ethylphenyl)₂P—CH(dimethylamino)CH(dimethylamino)-P(4-ethylphenyl)₂, and (2-ethylphenyl)₂P—CH(dimethylamino)CH(dimethylamino)-P(2-ethylphenyl)₂, but the present invention is not limited thereto.

The ligand having the P—N—P backbone structure of Formula 4 may be selected from (phenyl)₂PN(methyl)P(phenyl)₂, (phenyl)₂PN(pentyl)P(phenyl)₂, (phenyl)₂PN(phenyl)P(phenyl)₂, (phenyl)₂PN(p-methoxyphenyl)P(phenyl)₂, (phenyl)₂PN(p-tbutylphenyl)P(phenyl)₂, (phenyl)₂PN((CH₂)₃—N-morpholine)P(phenyl)₂, (phenyl)₂PN(Si(CH₃)₃)P(phenyl)₂, (((phenyl)₂P)₂NCH₂CH₂)N, (ethyl)₂PN(methyl)P(ethyl)₂, (ethyl)₂PN(isopropyl)P(phenyl)₂, (ethyl)(phenyl)PN(methyl)P(ethyl)(phenyl), (ethyl)(phenyl)PN(isopropyl)P(phenyl)₂, (phenyl)₂P(=Se)N(isopropyl)P(phenyl)₂, (phenyl)₂PCH₂CH₂P(phenyl)₂, (o-ethylphenyl)(phenyl)PN(isopropyl)P(phenyl)₂, (o-methylphenyl)₂PN(isopropyl)P(o-methylphenyl)(phenyl), (phenyl)₂PN(benzyl)P(phenyl)₂, (phenyl)₂PN(1-cyclohexylethyl)P(phenyl)₂, (phenyl)₂PN[CH₂CH₂CH₂Si(OMe₃)]P(phenyl)₂, (phenyl)₂PN(cyclohexyl)P(phenyl)₂, (phenyl)₂PN(2-methylcyclohexyl)P(phenyl)₂, (phenyl)₂PN(allyl)P(phenyl)₂, (2-naphthyl)₂PN(methyl)P(2-naphthyl)₂, (p-biphenyl)₂PN(methyl)P(p-biphenyl)₂, (p-methylphenyl)₂PN(methyl)P(p-methylphenyl)₂, (2-thiophenyl)₂PN(methyl)P(2-thiophenyl)₂, (phenyl)₂PN(methyl)N(methyl)P(phenyl)₂, (m-methylphenyl)₂PN(methyl)P(m-methylphenyl)₂, (phenyl)₂PN(isopropyl)P(phenyl)₂, and (phenyl)₂P(=S)N(isopropyl)P(phenyl)₂, but the present invention is not limited thereto.

The heteroatom ligand constituting the olefin oligomerization catalyst according to the present invention may be prepared using various methods known to those skilled in the art.

The olefin oligomerization catalyst according to the present invention may be mononuclear or binuclear. Specifically, the olefin oligomerization catalyst may be represented by $ML^1(L^2)_p(X)_q$ or $M_2X^1{}_2L^1{}_2(L^2)_y(X)_z$, wherein M is a transition metal, $L^1$ is a heteroligand, $L^2$ is an organic ligand, X and $X^1$ are each independently a halogen, p is an integer of 0 or 1 or more, q is an integer of (oxidation number of M−p), y is an integer of 2 or more, and z is an integer of (2×oxidation number of M)−y−2.

Preferably, the oligomerization catalyst according to one exemplary embodiment of the present invention may be represented by the following Formula 5 or 6, but the present invention is not limited thereto:

[Formula 5]

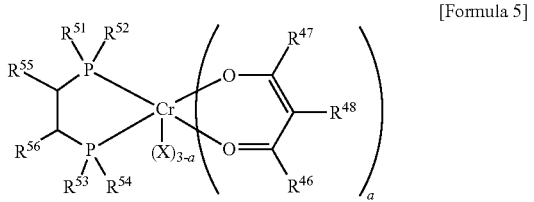

[Formula 6]

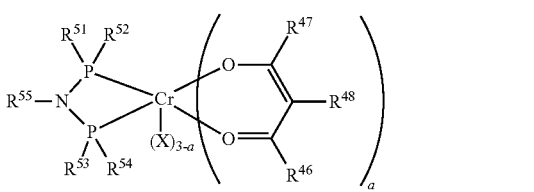

(wherein $R^{46}$ to $R^{48}$ are each independently hydrogen, a halogen, a (C6-C20)aryl, a (C6-C20)ar(C1-C10)alkyl, a (C1-C10)alkyl, a halo(C1-C10)alkyl, a (C6-C20)ar(C2-C10)alkenyl, a (C2-C10)alkenyl, a (C6-C20)ar(C2-C10)alkynyl, a (C2-C10)alkynyl, a (C1-C10)alkoxy, a (C6-C20)aryloxy, a (C1-C10)alkylcarbonyloxy, a (C2-C10)alkenylcarbonyloxy, a (C2-C10)alkynylcarbonyloxy, a (C3-C7)cycloalkyl, a (C1-C10)alkylsilyl, a (C2-C10)alkenylsilyl, a (C2-C10)alkynylsilyl, a (C6-C20)arylsilyl, a (C3-C20)heteroaryl, or a 5- to 7-membered heterocycloalkyl;

the aryl, the aralkyl, the alkyl, the aralkenyl, the alkenyl, the aralkynyl, the alkynyl, the alkoxy, the aryloxy, the cycloalkyl, the heteroaryl, and the heterocycloalkyl of $R^{46}$, $R^{47}$, and $R^{48}$ may be further substituted with one or more selected from a (C1-C10)alkyl, a (C2-C10)alkenyl, a (C2-C10)alkynyl, a (C1-C10)alkoxy, a (C6-C20)aryl, a (C6-C20)aryloxy, and a halogen;

$R^{51}$ to $R^{54}$ are each independently a (C6-C20) aryl, a (C6-C20)ar(C1-C10)alkyl, a (C6-C20)ar(C2-C10)alkenyl, a (C6-C20)ar(C2-C10)alkynyl, a (C1-C10)alkyl, a (C2-C10)alkenyl, a (C2-C10)alkynyl, a (C1-C10)alkoxy, a (C6-C20)aryloxy, a (C1-C10)alkoxycarbonyl, a (C1-C10)alkylcarbonyloxy, a (C2-C10)alkenylcarbonyloxy, a (C2-C10)alkynylcarbonyloxy, an aminocarbonyl, a (C1-C10)alkylcarbonylamino, a (C2-C10)alkenylcarbonylamino, a (C2-C10)alkynylcarbonylamino, a (C3-C7)cycloalkyl, a thio(C1-C10)alkyl, a thio(C2-C10)alkenyl, a thio(C2-C10)alkynyl, a (C1-C10)alkylsilyl, a (C2-C10)alkenylsilyl, a (C2-C10)alkynylsilyl, a (C6-C20)arylsilyl, a (C3-C20)heteroaryl, a 5- to 7-membered heterocycloalkyl, or —$NR^{21}R^{22}$, wherein $R^{21}$ and $R^{22}$ are each independently a (C1-C10) alkyl, a (C2-C10)alkenyl, a (C2-C10)alkynyl, a (C6-C20)aryl, a di(C1-C10)alkylamino, a di(C2-C10)alkenylamino, or a di(C2-C10)alkynylamino;

$R^{55}$ and $R^{56}$ are each independently a (C6-C20)aryl, a (C6-C20)ar(C1-C10)alkyl, a (C6-C20)ar(C2-C10)alkenyl, a (C6-C20)ar(C2-C10)alkynyl, a (C1-C10)alkyl, a (C2-C10)alkenyl, a (C2-C10)alkynyl, a (C3-C7)cycloalkyl, a (C3-C20)heteroaryl, a 5- to 7-membered heterocycloalkyl, a (C1-C10)alkoxy, a (C6-C20)aryloxy, a (C1-C10)alkoxycarbonyl, a (C1-C10)alkylcarbonyloxy, a (C2-C10)alkenylcarbonyloxy, a (C2-C10)alkynylcarbonyloxy, an aminocarbonyl, a (C1-C10)alkylcarbonylamino, a (C2-C10)alkenylcarbonylamino, a (C2-C10)alkynylcarbonylamino, a di(C1-C10)alkylamino, a di(C2-C10)alkenylamino, a di(C2-C10)alkynylamino, a (C1-C10)alkylsilyl, a (C2-C10)alkenylsilyl, a (C2-C10)alkynylsilyl, or a (C6-C20)arylsilyl, or $R^{45}$ and $R^{46}$ may be taken together via a (C3-C10)alkylene or a (C3-C10)alkenylene to form a ring;

the aryl, the aralkyl, the aralkenyl, the aralkynyl, the alkyl, the alkenyl, the alkoxy, the aryloxy, the alkoxycarbonyl, the alkylcarbonyloxy, the alkenylcarbonyloxy, the alkynylcarbonyloxy, the cycloalkyl, the heteroaryl, or the heterocycloalkyl of $R^{51}$ to $R^{54}$, and the aryl, the aralkyl, the aralkenyl, the aralkynyl, the alkyl, the alkenyl, the cycloalkyl, the heteroaryl, the heterocycloalkyl, the alkoxy, the aryloxy, the alkoxycarbonyl, the alkylcarbonyloxy, the alkenylcarbonyloxy, the alkynylcarbonyloxy, the aminocarbonyl, the alkylcarbonylamino, the alkenylcarbonylamino, the alkynylcarbonylamino, the dialkylamino, the dialkenylamino, the dialkynylamino, the alkylsilyl, the alkenylsilyl, the alkynylsilyl, or the arylsilyl of $R^{55}$ and $R^{56}$ may be further substituted with one or more selected from a (C1-C10)alkyl, a (C2-C10)alkenyl, a (C2-C10)alkynyl, a (C1-C10)alkoxy, a (C6-C20)aryloxy, a di(C1-C10)alkylamino, a di(C2-C10)alkenylamino, a di(C2-C10)alkynylamino, and a halogen;

X is a halogen; and
a is an integer of 0 or ranging from 1 to 3, b and c are each independently an integer of 1 or 2).

Preferably, the oligomerization catalyst may be compound in which $R^{46}$ to $R^{48}$ in Formulas 5 and 6 are each independently hydrogen, a (C1-C10)alkyl, or a halo(C1-C10)alkyl; $R^{51}$ to $R^{54}$ are each independently a (C6-C20) aryl; $R^{55}$ and $R^{56}$ may be each independently a (C1-C10) alkyl, or a compound in which $R^{51}$ to $R^{54}$ are each independently a (C6-C20) aryl; and $R^{55}$ and $R^{56}$ are each independently a (C1-C10)alkyl, and a is 0.

Hereinafter, preferred examples and comparative examples of the present invention will be described. However, it should be understood that the following examples are merely preferred examples of the present invention, and are not intended to limit the present invention.

PREPARATION EXAMPLE

As a catalyst for ethylene oligomerization, bis-[(S,S)-(phenyl)$_2$PCH(methyl)CH(methyl)P(phenyl)$_2$dichloride (µchloride)chromium] (5.3 µmol-Cr) was prepared according to the following method.

2.1 mg (5.3 umol) of chromium(III) trichloride tetrahydrofuran (CrCl$_3$(THF)$_3$) was dissolved in 1 mL of methane dichloride, and a solution obtained by dissolving 2.4 mg (5.6 umol) of an (S,S)-(phenyl)$_2$PCH(methyl)CH(methyl)P(phenyl)$_2$ ligand compound in 1 mL of methane dichloride was slowly added to the resulting solution, and reacted for 60 minutes. Thereafter, the resulting mixture was further stirred for 5 minutes, and 1.3 mg (5.6 umol) of sodium hexafluoroacetylacetonate was then slowly added to the mixture. Then, the reaction product was further stirred for 3 hours, and then filtered using a 0.2 um syringe filter. The resulting filtrate was dried under vacuum to remove volatile matters, thereby obtaining dried dark green solids, which were then used as the oligomerization catalysts of Examples and Comparative Examples as will be described below.

This catalyst is a catalyst having very excellent ethylene oligomerization reaction activity and selectivity, and may be identified more clearly with reference to Korean Patent Application No. 10-2016-0065709.

EXAMPLE 1

A 2,000 mL stainless steel pressure reactor was washed with nitrogen under vacuum, and 1 L of methylcyclohexane (MCH) was then put into the reactor. Modified methylaluminoxane (m-MAO3A, Akzo Nobel, 18% by weight in heptane) (1.57 g, 4 mmol) as a cocatalyst was sequentially put into the reactor, and a temperature of the reactor was then increased to 60° C.

Thereafter, 3.1 mg of bis-[(S,S)-(phenyl)$_2$PCH(methyl) CH(methyl)P(phenyl)$_2$dichloride(µ-chloride)chromium] (5.3 µmol-Cr) prepared in Preparation Example was put into the reactor, and the reactor was then filled with ethylene until the pressure in the reactor reached 20 bar. Then, ethylene was continuously fed to the reactor while maintaining the pressure in the reactor, and an oligomerization reaction was performed while stirring at 250 rpm for 2 hours. Subsequently, the stirring was stopped, all the gas-phase ethylene in the reactor was discharged, and the temperature of the reactor was lowered to 10° C.

Next, $CO_2$ gas serving as the catalyst inactivator was added at a pressure of 1 bar for 10 minutes using a dip tube to bubble a reaction solution, and the reaction was then stopped. Thereafter, the reaction product was filtered and separated. Then, 20 mL of the filtered product was dried at 100° C. for an hour in a separate flask, and then subjected to GC-FID analysis using heptane as the internal standard, and the purity of 1-octene was confirmed. The results are summarized in the following Table 1. The amount (based on the number of moles) of $CO_2$ introduced was 5 times higher than the total number of moles of aluminum in the cocatalyst.

EXAMPLE 2

A reaction product was obtained in the same manner as in Example 1, except that CO gas was used instead of the $CO_2$ gas. 20 mL of the filtered product was heated to 100° C. for an hour in a separate flask. GC-FID analysis was performed using heptane as the internal standard, and a change in purity of 1-octene was confirmed. The results are summarized in the following Table 1.

EXAMPLE 3

A reaction product was obtained in the same manner as in Example 1, except that an $O_2/N_2$ mixed gas (5% by weight of $O_2$ and 95% by weight of $N_2$) was used instead of the $CO_2$ gas. 20 mL of the filtered product was heated to 100° C. for an hour in a separate flask. GC-FID analysis was performed using heptane as the internal standard, and a change in purity of 1-octene was confirmed. The results are summarized in the following Table 1.

EXAMPLE 4

To evaluate the separation efficiency of the produced linear alpha olefins (LAOs) according to the type of the catalyst inactivator, a process for separating a catalyst deactivator was simulated using ASPEN PLUS V8.8 (AspenTech). Assuming that up to C20 components were also used as the product, after $CO_2$ gas serving as the catalyst inactivator was added to a reactor effluent, compositions of a mixture flowing in the first distillation column of five distillation columns to separate products according to the boiling points thereof were set as listed in the following Table 2. The number of distillation column stages was set to 50. The heat duty (MMkcal/hr, 1 MMkcal=$10^6$ kcal) of the condenser required to separate the catalyst inactivator in the mixture at 0.1% or less, the heat duty (MMkcal/hr) required for the reheater, and the purity of the reaction product were calculated. The results are summarized in Table 3.

EXAMPLE 5

To confirm the purity of the reaction product and evaluate the separation efficiency of the catalyst inactivator, a separation process was simulated in the same manner as in Example 4, except that CO gas was used as the catalyst inactivator after the oligomerization reaction. The results are summarized in Table 3.

EXAMPLE 6

To confirm the purity of the reaction product and evaluate the separation efficiency of the catalyst inactivator, a separation process was simulated in the same manner as in Example 4, except that an $O_2$ (5% by weight)/$N_2$ (95% by weight) gas was used as the catalyst inactivator after the oligomerization reaction. The results are summarized in Table 3.

COMPARATIVE EXAMPLE 1

A reaction product was obtained in the same manner as in Example 1, except that the $CO_2$ gas was not used. 20 mL of the filtered product was heated to 100° C. for an hour in a separate flask. GC-FID analysis was performed using heptane as the internal standard, and a change in purity of 1-octene was confirmed. The results are summarized in the following Table 1.

COMPARATIVE EXAMPLE 2

The purity of the reaction product was determined in the same manner as in Example 4, except that 2-ethyl-1-hexanol was used as the catalyst deactivator after the oligomerization reaction in a process simulation. Thereafter, the separation efficiency of the catalyst inactivator was evaluated. The results are summarized in Table 3. In the process simulation, because the boiling point of 2-ethylhexanol was distributed between the components to be separated, another two distillation columns had to be used, and the number of stages each of the seven distillation columns was set to 50.

TABLE 1

|  | Inactivator | Pressure/ time | Purity (%, 1-octene/ total C8) of 1-octene after heating |
| --- | --- | --- | --- |
| Example 1 | $CO_2$ | 1 bar/ 10 minutes | 98.93% |
| Example 2 | CO | 1 bar/ 10 minutes | 98.91% |
| Example 3 | $O_2$ (5% by weight)/ $N_2$ (95% by weight) | 1 bar/ 10 minutes | 98.88% |
| Comparative Example 1 | None | — | 95.72% |

TABLE 2

|  | Example 4 | Example 5 | Example 6 | Comparative Example 2 |
| --- | --- | --- | --- | --- |
| Solvent (% by weight) | 65.2 | 65.2 | 65.2 | 65.2 |
| Lights (~C4) (% by weight) | 8.8 | 8.8 | 8.8 | 8.8 |
| C6 alpha olefin (% by weight) | 5.7 | 5.7 | 5.7 | 5.7 |
| C8 alpha olefin (% by weight) | 11.3 | 11.3 | 11.3 | 11.3 |
| Heavy alpha olefins (C10+) (% by weight) | 9.0 | 9.0 | 9.0 | 9.0 |
| Catalyst inactivator | 5 equivalents based on the number of moles of Al in cocatalyst | 5 equivalents based on the number of moles of Al in cocatalyst | 5 equivalents based on the number of moles of Al in cocatalyst | 5 equivalents based on the number of moles of Al in cocatalyst |

TABLE 3

|  |  | Example 4 | Example 5 | Example 6 | Comparative Example 2 |
| --- | --- | --- | --- | --- | --- |
| Number of distillation columns |  | 5 | 5 | 5 | 7 |
| Purity (%) of 1-hexene in oligomerization reaction product |  | 98.84 | 98.84 | 98.84 | 98.84 |
| Purity (%) of 1-octene in oligomerization reaction product |  | 99.40 | 99.40 | 99.40 | 98.90 |
| Evaluation of separation efficiency of catalyst inactivator | Condenser heat duty (MMkcal/hr) | −13.36 | −13.36 | −13.36 | −14.12 |
|  | Reheater heat duty (MMkcal/hr) | 14.55 | 14.54 | 14.54 | 15.33 |

In Table 1, it can be seen that the purity of 1-octene in the oligomerization reaction product was high in all Examples 1 to 3, compared to that of Comparative Example 1.

Table 3, when the linear alpha olefins and the catalyst inactivator were separated by distillation, the heat duties required for the condenser and the reheater in Comparative Example 2 were very higher than those of Examples, and a larger number of distillation columns were required to prepare the same product because the boiling point of 2-ethylhexanol was distributed between the components to be separated, compared to those of Examples. That is, it can be seen that the heat duties required for the condenser and the reheater were higher than those of Examples even when a larger number of distillation columns were used. Accordingly, increases in the process energy and the number of distillation columns required to separate the catalyst inactivator from the product were inevitable in the case of Comparative Example 2, which resulted in severely degraded economic feasibility of a process and highly lowered actual industrial applicability.

Also, in Table 3, the purity of the finally separated 1-octene was higher in the case of Examples 4 to 6, compared to that of Comparative Example 2.

Accordingly, it was confirmed that the catalyst inactivator of the present invention had very excellent separation efficiency from the oligomerization reaction product, compared to those of Comparative Examples. From these results, the catalyst inactivator of the present invention is expected to remarkably reduce processing costs because the present invention may achieve high efficiency and a high added value of an ethylene oligomerization reaction, and is applicable to actual industries.

The invention claimed is:

1. A method for oligomerizing olefins, the method comprising the steps of:
    introducing an oligomerization transition metal catalyst, a cocatalyst, an olefin monomer, and a solvent into a reactor to perform an olefin oligomerization reaction and produce a reaction product comprising oligomers, wherein the transition metal catalyst is represented by $ML^1(L^2)_p(X)_q$ or $M_2X^1{}_2(L^2)_y(X)_z$, wherein M is a transition metal, $L^1$ is a heteroligand, $L^2$ is an organic ligand, X and $X^1$ are each independently a halogen, p is an integer of 0 or 1 or more, q is an integer of (oxidation number of M-p), y is an integer of 2 or more, and z is an integer of (2 x oxidation number of M) —y, and wherein 1-octene is included at 30% by weight or more, based on 100% by weight of linear alpha olefins in the reaction product of the oligomerization reactor;
    introducing a catalyst inactivator, which includes an oxygen-containing inorganic material in a gas phase, to the reaction product of the oligomerization reaction, wherein the oxygen-containing inorganic material is $O_2$, $CO_2$, CO, $H_2O$, $NO_x$, $SO_x$, or a mixture thereof; and
    separating the oligomers from the reaction product of the oligomerization reaction.

2. The method of claim 1, wherein the oxygen-containing inorganic material is in a gas phase at 25° C. and 1 atmospheric pressure (atm).

3. The method of claim 1, wherein the oxygen-containing inorganic material is $O_2$ or $CO_2$.

4. The method of claim 1, wherein the catalyst inactivator includes 0.5 to 100% by weight of the oxygen-containing inorganic material.

5. The method of claim 1, wherein the introducing of the catalyst inactivator is performed at 80° C. to 100° C.

6. The method of claim 1, further comprising, after the introducing of the catalyst inactivator:
    subjecting a gel- or solid-phase component including an inactivated catalyst to solid-liquid separation.

7. The method of claim 1, further comprising, after the introducing of the catalyst inactivator:
    separating an unreacted catalyst inactivator by distillation or adsorption.

8. The method of claim 1, further comprising:
    recirculating at least a portion of the reaction product including an unreacted olefin monomer present in the step of introducing of the catalyst inactivator, to the step of performing the oligomerization reaction.

9. The method of claim 8, wherein, in the recirculating of at least a portion of the reaction product, the catalyst inactivator in the reaction product including the unreacted olefin monomer is removed by adsorption.

10. The method of claim 1, wherein the cocatalyst is an aluminum compound, an organoaluminoxane, an organoboron compound, or a mixture thereof.

11. The method of claim 10, wherein an amount of the introduced catalyst inactivator is such an amount that an amount of the oxygen-containing inorganic material in the catalyst inactivator is 1 to 50 times higher than the total number of moles of aluminum, boron, or a combination thereof in the cocatalyst based on the number of moles.

12. The method of claim 1, wherein the olefin monomer is ethylene, and the oligomers include a mixture of C4-C40 linear alpha olefins.

* * * * *